(12) United States Patent
Wang et al.

(10) Patent No.: US 9,475,843 B2
(45) Date of Patent: Oct. 25, 2016

(54) ANTIMICROBIAL PEPTIDE WY-21 AND APPLICATION THEREOF

(71) Applicant: Zhejiang University, Hangzhou, Zhejiang Province (CN)

(72) Inventors: Yizhen Wang, Hangzhou (CN); Hongbo Yi, Hangzhou (CN)

(73) Assignee: Zhejiang University, Hangzhou, Zhejiang (CN)

( * ) Notice: Subject to any disclaimer, the term of this patent is extended or adjusted under 35 U.S.C. 154(b) by 0 days.

(21) Appl. No.: 15/164,028

(22) Filed: May 25, 2016

(65) Prior Publication Data

US 2016/0257718 A1 Sep. 8, 2016

Related U.S. Application Data

(63) Continuation of application No. PCT/CN2016/073390, filed on Feb. 3, 2016.

(30) Foreign Application Priority Data

Feb. 6, 2015 (CN) .......................... 2015 1 0065017

(51) Int. Cl.
*A61K 38/16* (2006.01)
*C07K 14/00* (2006.01)
*A61K 38/00* (2006.01)

(52) U.S. Cl.
CPC ............... *C07K 14/00* (2013.01); *A61K 38/00* (2013.01)

(58) Field of Classification Search
CPC .............................. A61K 38/16; C07K 14/00
USPC .................... 514/21.4, 2.3, 2.4, 2.8; 530/326
See application file for complete search history.

(56) References Cited

U.S. PATENT DOCUMENTS 8,389,679 B2 * 3/2013 Eckert .................... A01N 25/10
424/134.1
2010/0316643 A1 * 12/2010 Eckert .................... A01N 25/10
424/134.1

FOREIGN PATENT DOCUMENTS

| CN | 101081864 A | 12/2007 |
| CN | 103333225 A | 10/2013 |
| CN | 104628829 A | 5/2015 |

OTHER PUBLICATIONS

SEQ ID No. 1405 from U.S. Pat. No. 8,389,679 or US 20100316643, p. 1. Mar. 2013.*
State Intellectual Property Office of the People's Republic of China (ISR/CN), "International Search Report for PCT/CN2016/073390", China, May 5, 2016.

* cited by examiner

*Primary Examiner* — Julie Ha
(74) *Attorney, Agent, or Firm* — Shuang Chang; PSK Intellectual Property Group, LLC

(57) ABSTRACT

An antimicrobial peptide WY-21 has amino acid sequence of Val-Lys-Phe-Phe-Arg-Lys-Leu-Lys-Lys-Ser-Val-Lys-Glu-Lys-Ile-Gly-Lys-Glu-Phe-Lys-Arg (SEQ ID NO: 1). The antimicrobial peptide WY-21 can be used as broad-spectrum antibacterial agents for the treatment of Gram-negative or Gram-positive bacterial infection. It can also be applied for reducing immune system regulated inflammation.

5 Claims, 3 Drawing Sheets

SEQUENCE LISTING

<160> NUMBER OF SEQ ID NOS: 5

<210> SEQ ID NO 1
<211> LENGTH: 21
<212> TYPE: PRT
<213> ORGANISM: Artificial Sequence
<220> FEATURE:
<223> OTHER INFORMATION: antimicrobial peptides WY-21

<400> SEQUENCE: 1

Val Lys Phe Phe Arg Lys Leu Lys Lys Ser Val Lys Glu Lys Ile Gly
1               5                   10                  15

Lys Glu Phe Lys Arg
            20

<210> SEQ ID NO 2
<211> LENGTH: 37
<212> TYPE: PRT
<213> ORGANISM: Artificial Sequence
<220> FEATURE:
<223> OTHER INFORMATION: antimicrobial peptides LL-37

<400> SEQUENCE: 2

```
Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
        35

<210> SEQ ID NO 3
<211> LENGTH: 15
<212> TYPE: PRT
<213> ORGANISM: Artificial Sequence
<220> FEATURE:
<223> OTHER INFORMATION: antimicrobial peptides C-BF15

<400> SEQUENCE: 3

Val Lys Arg Phe Lys Lys Phe Phe Arg Lys Leu Lys Lys Ser Val
1               5                   10                  15

<210> SEQ ID NO 4
<211> LENGTH: 18
<212> TYPE: PRT
<213> ORGANISM: Artificial Sequence
<220> FEATURE:
<223> OTHER INFORMATION: antimicrobial peptides PG-1

<400> SEQUENCE: 4

Arg Gly Gly Arg Leu Cys Tyr Cys Arg Arg Arg Phe Cys Val Cys Val
1               5                   10                  15

Gly Arg

<210> SEQ ID NO 5
<211> LENGTH: 27
<212> TYPE: PRT
<213> ORGANISM: Artificial Sequence
<220> FEATURE:
<223> OTHER INFORMATION: antimicrobial peptides CP-1

<400> SEQUENCE: 5

Ser Trp Leu Ser Lys Thr Ala Lys Lys Leu Glu Asn Ser Ala Lys Lys
1               5                   10                  15

Arg Ile Ala Ile Ala Ile Gln Gly Gly Pro Arg
            20                  25
```

ANTIMICROBIAL PEPTIDE WY-21 AND APPLICATION THEREOF

CROSS-REFERENCE TO RELATED APPLICATION

This application is a continuation application of International Patent Application No. PCT/CN2016/073390, filed Feb. 3, 2016, which itself claims the priority to Chinese Patent Application No. 201510065017.X, filed Feb. 6, 2015 in the State Intellectual Property Office of P.R. China, which are hereby incorporated herein in their entireties by reference.

FIELD OF THE INVENTION

The present invention relates generally to the field of biomedical technology, more particularly to an antimicrobial peptide WY-21 and its application.

BACKGROUND OF THE INVENTION

Antibiotics misuse leads to acquired bacterial resistance, residues in animal products, and environmental pollution. Due to the increased severity of the acquired bacterial resistance, many antibiotics have become ineffective against pathogens. Moreover, antibiotics disrupt intestinal flora and innate immunity in host intestines. Therefore, it has become an urgent need to search for safe and highly effective antimicrobial agents.

Antimicrobial Peptides (AMPs) are important components of innate immunity system against invasion by bacterial pathogens. AMPs have broad-spectrum antimicrobial activities, functioning through mechanisms of membrane disruption, thus are not prone to develop bacterial resistance. AMPs also possess a variety of biological functions, such as stimulation of cell proliferation, activation of the immune system, anti-viral, anti-obesity, and anti-inflammation. As a result, in recent years, a great deal of attention has been attracted to use AMPs as templates for designing new antimicrobial agents. Thus, AMPs have become important breakthrough for the development of new and highly effective alternatives to antibiotics.

α-helical AMPs are the most commonly existing AMPs. The α-helix structure generally contains both hydrophilic residues and hydrophobic residues, and thus possesses amphiphilic properties. Helical AMPs generally do not have significant structural features in the aqueous phase, but exhibit α-helix structure in the lipid-rich cell membrane environment. These types of AMPS exhibit bactericidal effects primarily by disrupting the bacterial cell membrane, leading to gradual degradation of the membrane electrolyte or other signal substances. However, a lot of natural antibacterial peptides are immunogenic, show low antibacterial activity, are unstable, have strong cytotoxicity or high hemolysis, limiting their applications as antimicrobial agents. Therefore, small molecular weight, high antibacterial activity, safety and stability are key factors in achieving the purpose of using antimicrobial peptides to partially replace antibiotics.

SUMMARY OF THE INVENTION

One of the objectives of the present invention is to provide a safe and highly effective antimicrobial peptide WY-21, and its application, so as to solve the problems existing in the current development of using natural antibacterial peptides.

One aspect of the present invention provides an antimicrobial peptide WY-21, and provides its sequence as Val-Lys-Phe-Phe-Arg-Lys-Leu-Lys-Lys-Ser-Val-Lys-Glu-Lys-Ile-Gly-Lys-Glu-Phe-Lys-Arg (SEQ ID NO:1).

In another aspect of the present invention, the antimicrobial peptide WY-21 is an artificial synthetic α helix cationic peptide with 21 amino acid residues, molecular weight of 2624.2 dalton (Da), isoelectric point of 10.79, and net charge of +8.

In yet another aspect of the present invention, the antimicrobial peptide WY-2 is used for preparation of broad-spectrum antibacterial agents for the treatment of Gram-negative or Gram-positive bacterial infections. Gram-negative bacteria include *E. coli* ATCC25922, *E. coli* K88, *E. coli* K12, *E. coli* EPEC 078:K80, *E. coli* EPEC 0144:K26, *E. coli* EPEC 044:K74, *S. choleraesuis* CMCC50020, *S. typhimurium* CMCC50013, *S. enteritidis* CMCC50041, *P. aeruginosa* CMCC27853. Gram-positive bacteria include *S. aureus* ATCC25923 and *S. epidermidis* ATCC12228.

In yet another aspect of the present invention, the antimicrobial peptide WY-2 is used for preparation of drugs for reducing inflammation by immune regulation.

For the instructions and dosage of antimicrobial peptide WY-21 in the present invention, please refer to the instructions and dosage for conventional antimicrobial peptides (especially those with broad-spectrum antimicrobial activities against Gram-negative or Gram-positive bacterial infections), such as PG-1 and CP-1, etc.

The synthesized antimicrobial peptide WY-21 in the present invention possesses characteristics of a α helical peptide with short-chain cationic, high stability, and convenient for synthesis. The amino acid sequence of antimicrobial peptide WY-21 is not found in the National Center For Biotechnology Information (NCBI)'s protein database. Antimicrobial peptide WY-21 has a high net charge, broad-spectrum antimicrobial activity, high anti-bacterial activity, low hemolytic activity and cytotoxicity, and can play a role in immune regulation to reduce inflammation.

The above illustration is only a summary of the technical solutions of the present invention. In order to enable the technical means of the present invention to be understood more clearly, implementation may be performed according to contents of the specification. In order to make the above and other objectives, features, and advantages of the present invention more comprehensible, detailed illustration is provided below through preferred embodiment with reference to the accompanying drawings.

BRIEF DESCRIPTION OF THE DRAWINGS

The accompanying drawings illustrate one or more embodiments of the invention and, together with the written description, serve to explain the principles of the invention. Wherever possible, the same reference numbers are used throughout the drawings to refer to the same or like elements of an embodiment. The drawings do not limit the present invention to the specific embodiments disclosed and described herein. The drawings are not necessarily to scale, emphasis instead being placed upon clearly illustrating the principles of the invention.

DETAILED DESCRIPTION OF THE INVENTION

Figure 1:
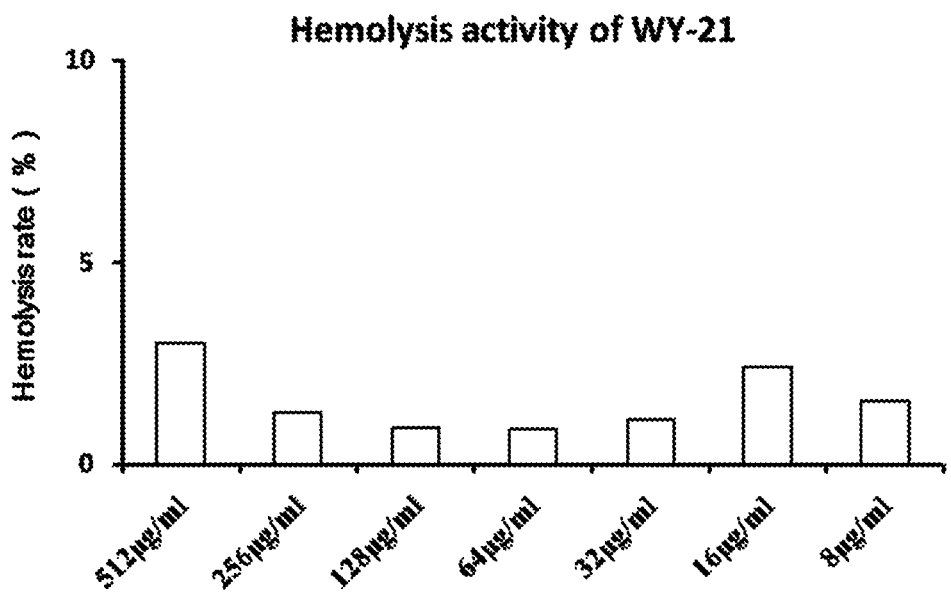
FIG. 1 shows the effects of antimicrobial peptide WY-21 on a variety of hemolysis rates of porcine erythrocyte. The result is an average of six independently repeated experiments.

The following description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. For purposes of clarity, the same reference numbers will be used in the drawings to identify similar elements.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. The use of examples anywhere in this specification, including examples of any terms discussed herein, is illustrative only, and in no way limits the scope and meaning of the disclosure or of any exemplified term. Likewise, the disclosure is not limited to various embodiments given in this specification.

As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise.

As used herein, the terms "comprising," "including," "having," "containing," "involving," and the like are to be understood to be open-ended, i.e., to mean including but not limited to.

The aforementioned and other technical contents, features, and effects of the present invention are clearly presented in the following detailed illustration of preferred embodiments below with reference to the reference drawings. Through illustration of the embodiments, the technical means adopted by the present invention to achieve the predetermined objective and the effects shall be understood more deeply and specifically. However, the accompanying drawings are only for reference and illustration, but are not intended to limit the present invention.

Embodiment 1

Preparation of Antimicrobial Peptide WY-21

In one embodiment of the present invention, an antimicrobial peptide WY-21 was synthesized from C-terminal to N-terminal one by one according to the amino acid sequence of SEQ ID NO:1 by solid phase chemical synthesis using an automated peptide synthesizer. The synthesized antimicrobial peptide WY-21 was purified by desalting using reverse phase high performance liquid chromatograph (HPLC). The purity of the purified WY-21 was evaluated by HPLC, and the evaluated purity is higher than 95%. Matrix Assisted Laser Desorption/Ionization-Time of Flight (MALDI-TOF) was used to determine the molecular weight of the antimicrobial peptide WY-21, and the determined molecular weight is consistent with the theoretical molecular weight. The amino acid sequence was confirmed by an automatic amino acid sequencer.

The synthesized antimicrobial peptide WY-21 contains 21 amino acid residues with a molecular weight of 2624.2 dalton (Da). Its complete sequence is Val-Lys-Phe-Phe-Arg-Lys-Leu-Lys-Lys-Ser-Val-Lys-Glu-Lys-Ile-Gly-Lys-Glu-Phe-Lys-Arg, as shown in SE ID NO:1.

TABLE 1

Physical and chemical parameters of the antimicrobial peptide WY-21.

| Item | WY-21 |
|---|---|
| Amino acid residues | 21 |
| Molecular weight | 2624.2 Da |
| Isoelectric point | 10.79 |
| Net charge | +8 |
| Grand average of hydropathy | −1.110 |
| Protein binding potential | 3.02 kcal/mol |
| Instability index | −1.02 |
| Total hydrophobic residues in the same surface | 6 |

As shown in Table 1, antimicrobial peptide WY-21 possesses characteristics of relatively low molecular weight, good stability, high positive net charge, low grand average hydropaty, and low instability index.

Embodiment 2

Minimum Inhibitory Concentration (MIC) Test of Antimicrobial Peptide WY-21

Bacteria was inoculated on Mueller-Hinton (MH) agar plate, the inoculated agar plate was inverted to grow single colonies. A single colony was inoculated in 3 mL MH broth, and the broth was cultured with constant shaking at constant temperature until turbid. 30 µL of bacterial suspension was then transferred to 3 mL of fresh MH broth, and the broth was cultured with shaking at constant temperature until $OD_{600} \approx 0.5$. 10 µL bacterial suspension was transferred to 10 mL fresh MH broth and then vortexed to mix well. Now the number of viable bacteria should be about $1 \times 10^5 \sim 5 \times 10^5$ CFU/mL, which is suitable for determining the MIC. For each testing well in a 96-well round bottom plate, 90 µL of bacterial suspension was added, and then 10 µL of double dilution antimicrobial peptide WY-21 was added, such that the testing wells have the peptide WY-21 with a final concentration of 256 µg/mL, 128 µg/mL, 64 µg/mL, 32 µg/mL, 16 µg/mL, 8 µg/mL, 4 µg/mL, 2 µg/mL, 1 µg/mL, 0.5 µg/mL, 0.25 µg/mL, respectively. In addition, 100 µL of bacterial suspension was added to a well as positive control, and 100 µL of MH broth was added to a well as negative control. Each testing condition and controls was performed with 6 repeats. After cultured for 24 hours (hrs) at 37° C. in an incubator, the bottom of each well was observed for bacterial precipitation. The minimum concentration of the WY-21 without bacterial precipitate was determined as MIC.

TABLE 2

WY-21 MICs against Gram-negative and Gram-positive bacteria

| Bacteria | WY-21 MIC (µg/ml) |
|---|---|
| Gram-negative bacteria | |
| E. coli ATCC25922 | 8 |
| E. coli K 88 | 8 |
| E. coli K 12 | 4 |
| E. coli EPEC O78:K80 | 16 |
| E. coli EPEC O144:K26 | 16 |
| E. coli EPEC O44:K74 | 8 |
| S. choleraesuis CMCC50020 | 16 |
| S. typhimurium CMCC50013 | 16 |
| S. enteritidis CMCC50041 | 64 |
| P. aeruginosa CMCC27853 | 8 |
| Gram-positive bacteria | |
| S. aureus ATCC25923 | 8 |
| S. epidermidis ATCC12228 | 32 |

In Table 2, the WY-21 MIC represents the minimum inhibitory concentration of the antimicrobial peptide WY-21. The above results are average of 6 independent experimental repeats.

As show in Table 2, antimicrobial peptide WY-21 possesses strong antibacterial activities against Gram-positive bacteria and Gram-negative bacteria.

Embodiment 3

Hemolysis Activity of Antimicrobial Peptide WY-21

Blood was collected from porcine vena cava with heparin added, and mixed with RPMI1640 medium at a volume ratio of 1:1. After centrifuging with FICOLL-PAQUE™, circular and milky peripheral blood mononuclear cells (PMBCs) were drawn for later use, and erythrocytes at the bottom were collected. The erythrocytes were washed with 1×PBS until the supernatant was colorless. Then the washed erythrocytes were diluted 90-fold (1:89) with 1×PBS to determine hemolysis activity.

90 µL working solution of erythrocytes was added to each well in 96-well plate, and then 10 µL antimicrobial peptide WY-21 with double dilution was added to each well, with final concentrations of 512 µg/mL, 256 µg/mL, 128 µg/mL, 64 µg/mL, 32 µg/mL, 16 µg/mL, 8 µg/mL and 4 µg/mL. Triton X-100 (final concentration 1%) was used as positive control, and 10 uL 1×PBS was used as negative control. Each group was performed with 6 replications. Cells were cultured for 24 hrs at 37° C. in a cell culture incubator, and followed by centrifugation at 1500 rpm for 20 min. Then supernatant was transferred to a new 96-well plate to measure the values of OD at 414 nm and 546 nm using a microplate reader, and ΔOD was calculated. The formula for calculating hemolysis ratio is as follows: hemolysis ratio (%)=100%*(ΔOD treatment group−ΔOD negative control)/(ΔOD positive control−ΔOD negative control).

FIG. 1 shows hemolysis activities of antimicrobial peptide WY-21 on porcine erythrocytes. As shown in FIG. 1, the antimicrobial peptide WY-21 exhibits low hemolysis activity on porcine erythrocytes. The hemolysis ratio of antimicrobial peptide WY-21 at a concentration of 512 µg/mL is less than 5%.

Embodiment 4

Cytotoxicity of Antimicrobial Peptide WY-21

Purified PBMCs were diluted to 1×10⁶ cells/mL, and cells were seeded with 90 uL per well in a 96-well plate. Further, background control well (100 µL RMPI1640 medium), low level control well (90 µL cell culture+10 µL PBS), and high level control well (90 µL cell culture+10 µL 20% Triton X-100) were also prepared. The 96-well plate was cultured at 37° C. for 2 hrs in a 5% $CO_2$ incubator. 10 µL of WY-21 was added to each well to final concentrations of 512 µg/mL, 256 µg/mL, 128 µg/mL, 64 µg/mL, 32 µg/mL, 16 µg/mL and 8 µg/mL, respectively. Each group of experiment (each concentration) was repeated for six replications. After culturing for 24 hrs, 10 µL TritonX-100 (20%) was added to each positive control well, and mixed by pipetting. The plate was further incubated for 15 min. After culturing, the cells were centrifuged at 1500 rpm for 10 min. 60 µL of supernatant was drawn carefully from the center of each well and transferred to corresponding wells of a transparent new 96-well plate. 30 uL of LDH diluent was added to each well. The plate was cultured at room temperature for 30 min with vibration in a dark environment. OD values were recorded at 492 nm and 900 nm using a microplate reader for calculating ΔOD value.

The formula for calculating LDH releasing rate is as follows: LDH releasing rate (%)=100%*(ΔOD treatment−ΔOD negative control)/(ΔOD negative control−ΔOD positive control).

Figure 2:
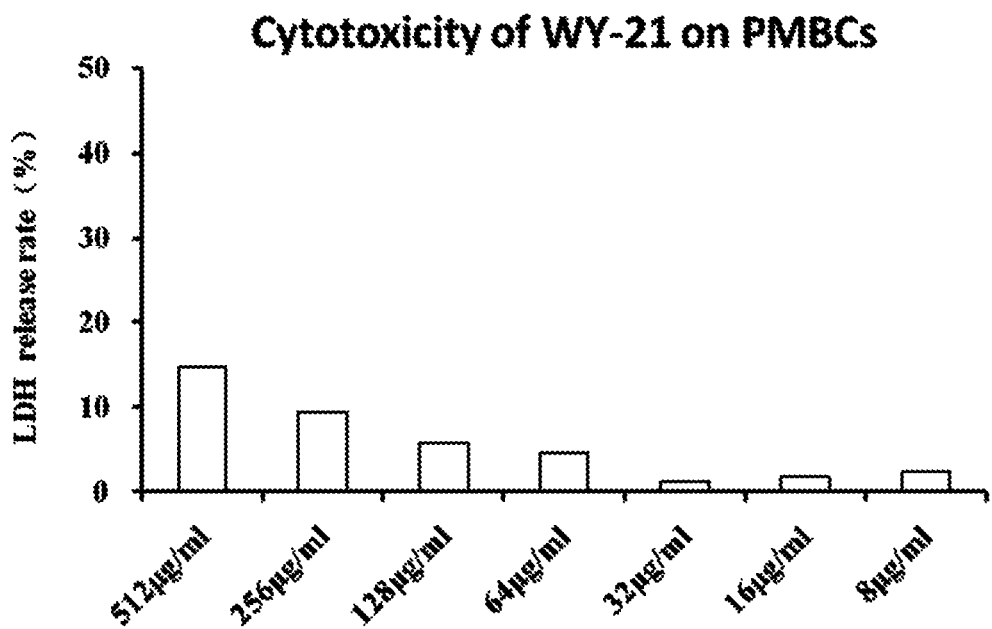
FIG. 2 shows the effect of antimicrobial peptide WY-21 on porcine PMBCs cytotoxicity. LDH indicates lactate dehydrogenase. The result is an average of six independently repeated experiments.

FIG. 2 shows the effect of antimicrobial peptide WY-21 on the LDH releasing rate of PBMCs. As shown in FIG. 2, LDH releasing rate of porcine peripheral mononuclear cells treated with WY-21 (≤256 µg/mL) was less than 10%, indicating that the cytotoxicity of antimicrobial peptide WY-21 is very low.

Embodiment 5

Antimicrobial Peptide WY-21 Acting as an Immune Regulator to Alleviate Inflammation Porcine macrophage cells (3D4/2 cell line) were cultured on RPMI-1640 medium with 10% fetal bovine serum, at 37° C. in a 5% $CO_2$ cell incubator, until the cells formed a monolayer with about 80-90% confluency. The cells were counted and plated. The cells were seeded to a 6-well plate at 1×10⁶/well, RPMI-1640 complete medium was added, and the cells were cultured to 80% confluency. Then the medium was replaced by fresh serum-free RPMI-1640 medium (2 mL). Cells were treated with groups of: PBS control, 20 µg/mL antimicrobial peptides WY-21, 1 µg/mL E. coli LPS, and 20 µg/mL WY-21+1 µg/mL E. coli LPS, respectively. Each group of experiments was repeated for six replications. After incubation for 24 hrs, cells were collected and total RNA was extracted using Trizol. cDNA was obtained by reverse transcription. Relative mRNA expression of IL-6, IL-8 and IL-22 was detected. The relative mRNA expression of IL-22, IL-8 and IL-6 were measured by quantitative fluorescence method. GAPDH gene was used as a internal reference gene.

Figure 3:
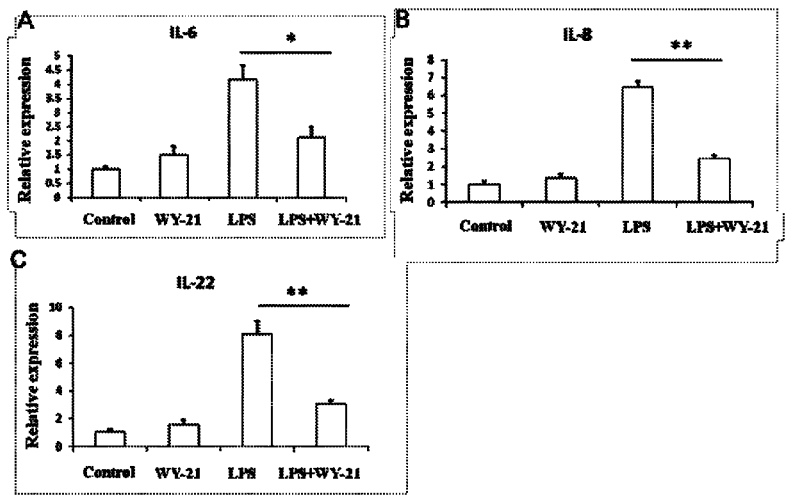
FIG. 3 shows the effect of antimicrobial peptide WY-21 on LPS-induced inflammation in porcine macrophages.

FIG. 3 shows effects of antimicrobial peptide WY-21 on LPS-induced inflammation in macrophages.

As shown in FIG. 3, the relative mRNA expressions of IL-6, IL-8 and IL-22 genes in macrophages of the WY-21 and LPS combined group were significantly decreased comparing with the LPS alone group, indicating that antimicrobial peptide WY-21 acts as an immune regulator to alleviate inflammation.

Comparative Examples

Furthermore, the amino acid sequence of antimicrobial peptide WY-21 was used to search against the NCBI protein database. Two proteins, LL-37 and Cathelicidin-BF15 (C-BF 15), were found to exhibit partial sequence similarity with WY-21. In addition, by searching literature, two antimicrobial peptides, PG-1 and CP-1, were also found to possess strong antibacterial activity. The aforementioned antimicrobial peptides were used as controls in the same experiments described in the second, third, fourth and fifth embodiments.

The followings are amino acid sequences of the aforementioned antimicrobial peptides:

LL-37:
(SEQ ID NO: 2)
Leu Leu Gly Asp Phe Phe Arg Lys Ser Lys Glu Lys
Ile Gly Lys Glu Phe Lys Arg Ile Val Gln Arg Ile
Lys Asp Phe Leu Arg Asn Leu Val Pro Arg Thr Glu
Ser;

C-BF15:
(SEQ ID NO: 3)
Val Lys Arg Phe Lys Lys Phe Phe Arg Lys Leu Lys
Lys Ser Val;

PG-1:
(SEQ ID NO: 4)
Arg Gly Gly Arg Leu Cys Tyr Cys Arg Arg Arg Phe
Cys Val Cys Val Gly Arg;

CP-1:
(SEQ ID: NO: 5)
Ser Trp Leu Ser Lys Thr Ala Lys Lys Leu Glu Asn
Ser Ala Lys Lys Arg Ile Ala Ile Ala Ile Gln Gly
Gly Pro Arg.

Figure 4:
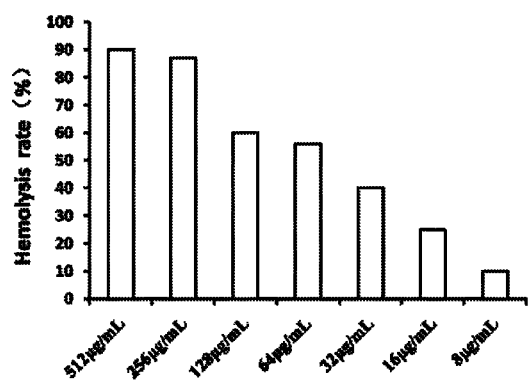
FIG. 4 shows the effect of antimicrobial peptide PG-1 on a variety of hemolysis rates of porcine erythrocyte.
Figure 5:
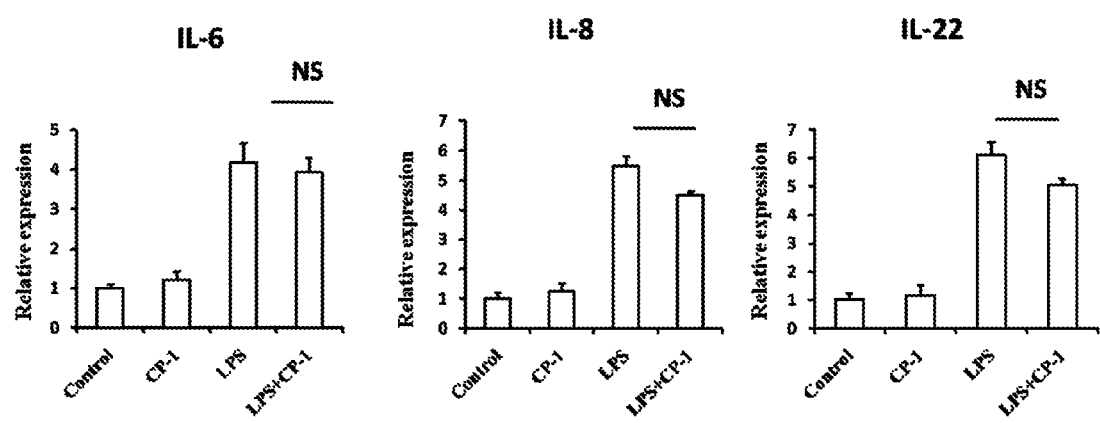
FIG. 5 shows the effect of antimicrobial peptide CP-1 on LPS-induced inflammation in macrophages.

As shown in the following Table 3, LL-37 and Cathelicidin-15 show some antibacterial activity but the antibacterial activity of LL-37 and Cathelicidin-15 is less than that of the WY-21. Antibacterial activity of PC-1 and CP-1 is similar to that of the WY-21. However, the hemolysis activity of PG-1 is higher than WY-21 (see FIG. 4). Further, CP-1 has no effects on LPS-induced inflammation, and the effect of reducing immune system regulated inflammation by CP-1 is much less than by the WY-21.

TABLE 3

Antibacterial activity of AMPS (MIC, μg/ml)

| Bacteria | LL-37 | C-BF15 | PG-1 | CP-1 |
|---|---|---|---|---|
| Gram-negative bacteria | | | | |
| E. coli ATCC25922 | 16 | 64 | 4 | 4 |
| E. coli K 88 | 32 | 32 | 8 | 4 |
| E. coli K 12 | 256 | 64 | 8 | 8 |
| E. coli EPEC O78:K80 | — | 128 | 16 | 16 |
| E. coli EPEC O144:K26 | — | 64 | 64 | 128 |
| E. coli EPEC O44:K74 | — | 64 | 32 | 32 |
| S. choleraesuis CMCC50020 | 128 | 256 | 4 | 8 |
| S. typhimurium CMCC50013 | 128 | 32 | 4 | 8 |
| S. enteritidis CMCC50041 | — | 64 | 16 | 16 |
| P. aeruginosa CMCC27853 | 128 | 128 | 8 | 16 |
| Gram-positive bacteria | | | | |
| S. aureus ATCC25923 | 16 | 16 | 2 | 128 |
| S. epidermidis ATCC12228 | 256 | 64 | 4 | 128 |

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to activate others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

What is claimed is:

1. An antimicrobial peptide, comprising the amino acid sequence of Val-Lys-Phe-Phe-Arg-Lys-Leu-Lys-Lys-Ser-Val-Lys-Glu-Lys-Ile-Gly-Lys-Glu-Phe-Lys-Arg (SEQ ID NO: 1).

2. The antimicrobial peptide of claim 1, wherein the antimicrobial peptide is a synthetic cationic peptide with an α-helix structure, 21 amino acid residues, a molecular weight of 2624.2 dalton (Da), isoelectric point of 10.79, and a net charge of +8.

3. An antibacterial agent, comprising the antimicrobial peptide of claim 1.

4. A method of treating Gram-positive or Gram-negative bacterial infection of a patient in need thereof, comprising administering the antibacterial agent of claim 3 to the patient.

5. A method of reducing immune system regulated inflammation of a patient in need thereof, comprising administering the antimicrobial peptide of claim 1 to the patient.

* * * * *